United States Patent [19]
Shaw et al.

[11] Patent Number: 5,330,716
[45] Date of Patent: Jul. 19, 1994

[54] FLEXIBLE PUSHER BLADE AND HOUSING

[75] Inventors: James D. Shaw, Hilton; Martin F. Muszak; David A. Heavner, both of Rochester, all of N.Y.

[73] Assignee: Eastman Kodak Company, Rochester, N.Y.

[21] Appl. No.: 590,205

[22] Filed: Sep. 28, 1990

Related U.S. Application Data

[63] Continuation-in-part of Ser. No. 500,650, Mar. 28, 1990, abandoned, which is a continuation-in-part of Ser. No. 349,451, May 9, 1989, abandoned.

[51] Int. Cl.⁵ ............................................. G01N 35/00
[52] U.S. Cl. ........................................ 422/63; 422/65; 422/66; 436/46
[58] Field of Search ................................ 422/63–67; 436/46; 414/19, 217, 331, 416, 417, 796.8; 221/232, 260, 275; 198/346, 468.8, 468.9, 753; 343/903

[56] References Cited

U.S. PATENT DOCUMENTS

| | | | |
|---|---|---|---|
| 4,512,952 | 4/1985 | Blanding et al. | 422/63 |
| 4,633,266 | 12/1986 | Alf et al. | 343/903 |
| 4,649,398 | 3/1987 | Yamamoto et al. | 343/903 |
| 4,907,007 | 3/1990 | Druecker et al. | 343/903 |

FOREIGN PATENT DOCUMENTS

| | | |
|---|---|---|
| 1297285 | 5/1962 | France . |
| 2419244 | 11/1979 | France . |
| 2-184761 | 7/1990 | Japan . |

OTHER PUBLICATIONS

Pull Strap of Racing Toy.

*Primary Examiner*—Lyle A. Alexander
*Attorney, Agent, or Firm*—Dana M. Schmidt

[57] ABSTRACT

A pusher blade and its housing are described, in which the blade has a stiff front end for engaging slide-type test elements, and a flexible body portion and back end. The housing forces the blade to curve through an angle, preferably about 90° C., to minimize the extension in one direction the blade would have if it were entirely rigid.

The housing can provide for separate stacks of elements in separate environments to be engaged by the blade, since sealing means are provided for preventing substantial intermixing of the environments when the blade is activated.

13 Claims, 6 Drawing Sheets

FIG. I
(PRIOR ART)
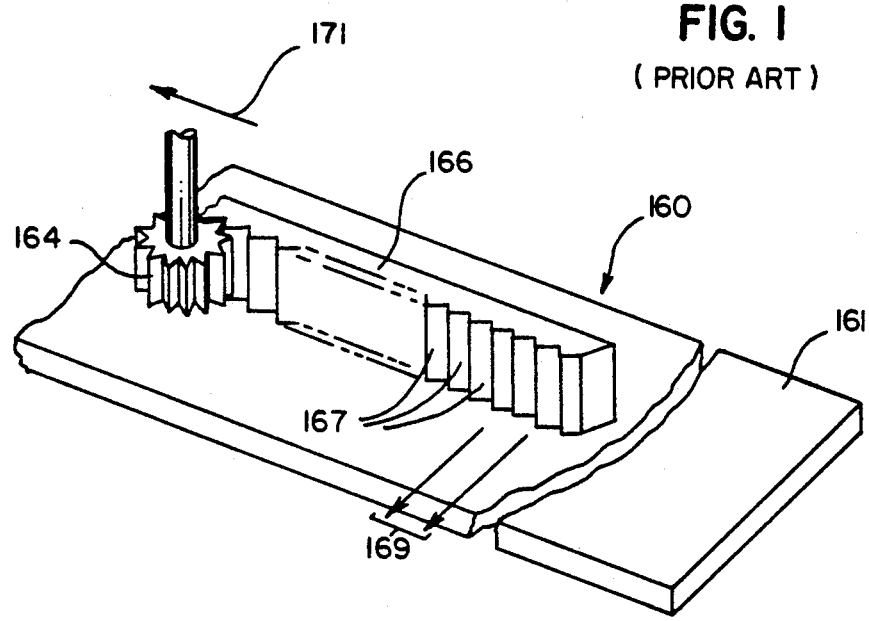
FIG. II
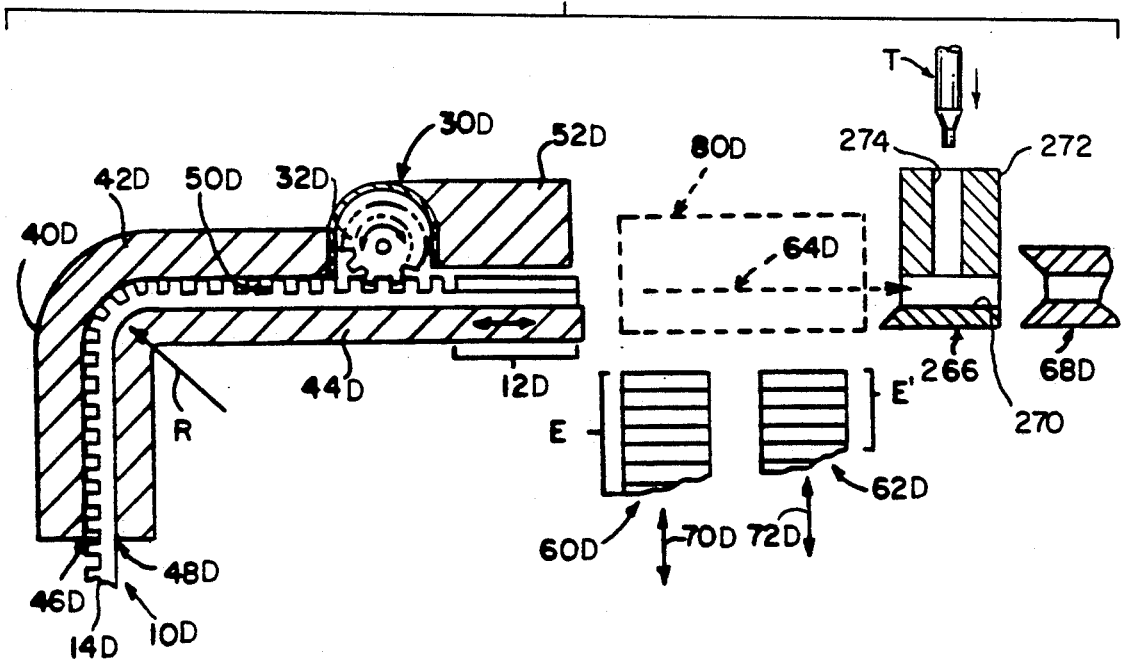

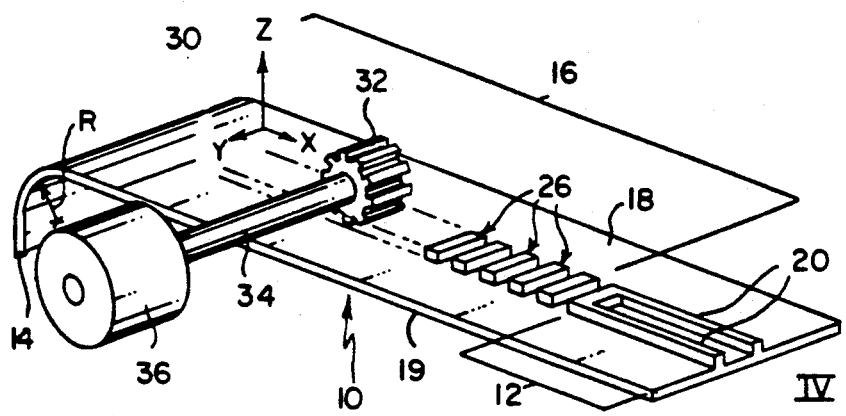
FIG. 2
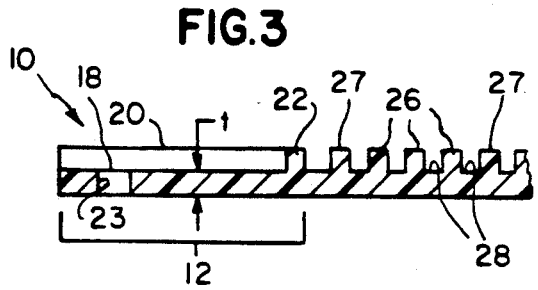
FIG. 3
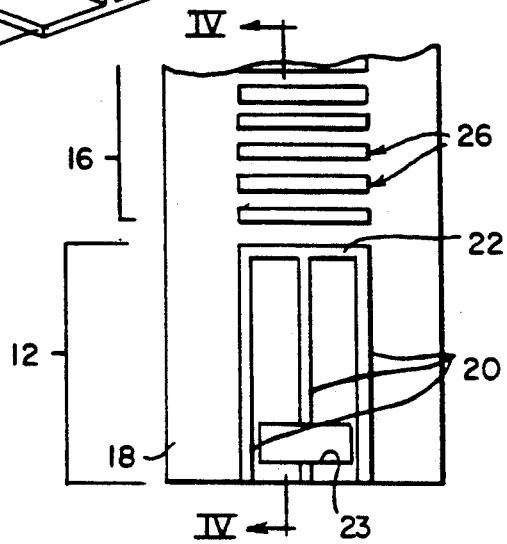
FIG. 4
FIG. 5
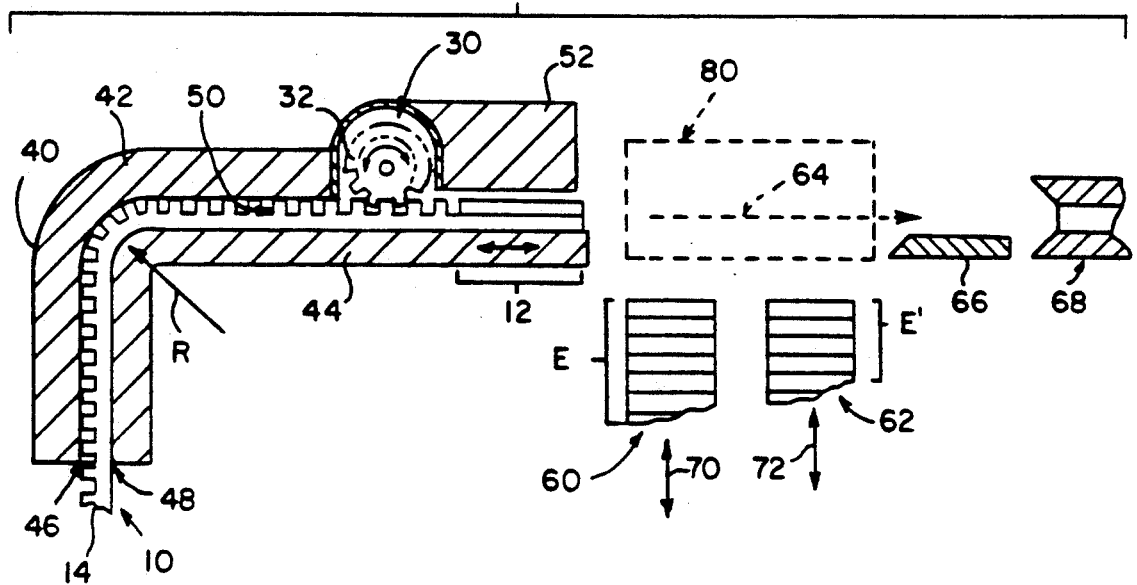

FLEXIBLE PUSHER BLADE AND HOUSING

RELATED APPLICATIONS

This is a continuation-in-part application of the U.S. Ser. No. 500,650 filed on Mar. 28, 1990, now abandoned which in turn is a continuation-in-part application of U.S. Ser. No. 349,451, filed on May 9, 1989, now abandoned.

FIELD OF THE INVENTION

The invention is directed to pusher blades for moving slide-like elements, particularly in analyzers.

BACKGROUND OF THE INVENTION

Pusher blades are the conventional mechanisms for moving slide-type test elements in an analyzer from one location to another. For example, such blades have been used to push a test element out of one or two stacks of elements, into another part of an analyzer so that the test element can be further processed to detect an analyte in a body liquid deposited on the test element. An example is pusher blade 60 in FIG. 4 of U.S. Pat. No. 4,512,952.

As such analyzers become more and more involved in their processing of the test elements, the blades must traverse greater and greater distances. For example, in the aforementioned patent, the blade must traverse not only one stack of elements to push an element out of such stack, but in addition, it must traverse a second adjacent stack that is an alternate supply of elements. The conventional construction for the blade in all such instances is a rigid one. This is due to the use of a ridge that provides a rack for a rack-and-pinion drive of the blade, as is explained hereinafter. Thus, the problem becomes one of providing sufficient, usually horizontal, space for a longer rigid blade to operate in. This in turn makes the analyzer longer or wider, just to accommodate such a long, rigid pusher blade.

Therefore, prior to this invention there has been a need for a pusher blade construction which will provide the longer traversals now being required of such blades, without unduly extending the dimensions of the analyzer just to accommodate a long, rigid blade.

SUMMARY OF THE INVENTION

I have constructed a pusher blade and associated housing that solve the aforementioned problems.

More specifically, in accord with one aspect of the invention there is provided a chemical analyzer including a pusher blade for transferring a test element from one location to another, the blade comprising a first relatively stiff end portion opposite to the first end portion, and a body portion between the end portions, at least the body portion and the second end portion being sufficiently flexible as to bend without exceeding its elastic limit, about a radius of curvature of no greater than about 20 cm.

In accord with another aspect of the invention, there is provided a chemical analyzer including a housing for a pusher blade, comprising opposing guiding side walls defining a path of travel for a pusher blade, the side walls being shaped to define an angled bend in such path, and means in the housing for driving the blade.

In accord with yet a further aspect of the invention, there is provided apparatus for supplying test elements from at least two stacks of test elements, to an analyzer, the apparatus including a pusher blade, means for moving and guiding the blade along a predetermined path, and means for holding the stacks in position to intersect the predetermined path. The apparatus is improved in that it includes wall means for separating the stacks within the housing into two separate environments, and means for preventing substantial intermixing of the separate environments of the separated stacks when the blade intersects either of the stacks along the path.

In accord with still another aspect of the invention, there is provided a pusher blade mechanism for pushing flat slide-like articles from one location to another, the mechanism including a flexible pusher blade, drive means for moving the blade towards and away from slide-like elements, and back-up means positioned opposite the drive means for keeping the blade engaged with the drive means, the back-up means including a clutch that allows the blade, in the presence of increased resistance, to disengage from the drive means, so that damage due to a jam is minimized.

Accordingly, it is an advantageous feature of the invention that a pusher blade is provided with a long traverse capability, without extending unduly the dimensions of the analyzer.

It is a related advantageous feature of the invention that a pusher blade and housing are provided that wrap the blade around the rest of the analyzer, thus conserving space.

Yet another advantageous feature of the invention is that such a pusher blade can be provided inexpensively.

A further advantageous feature is that such a pusher blade can operate with two different environments and not cause substantial intermixing of the environments.

Other advantageous features will become apparent upon reference to the following detailed Description of the Preferred Embodiments, when read in light of the attached drawings.

BRIEF DESCRIPTION OF THE DRAWINGS

FIG. 1 is a fragmentary perspective view of a prior art pusher blade, shown for comparative purposes;

FIG. 2 is a perspective view of a pusher blade constructed in accordance with the invention, together with its drive means;

FIG. 3 is a fragmentary elevational view of the stiff end of the pusher blade;

FIG. 4 is a section view taken generally along the line IV—IV of FIG. 3;

FIG. 5 is a fragmentary, partially schematic, elevational view, partially in section, illustrating the use of the invention in an analyzer;

FIG. 11 is an elevational view similar to that of FIG. 5, but illustrating a further alternate embodiment of the invention.

DESCRIPTION OF THE PREFERRED EMBODIMENTS

Figure 6:
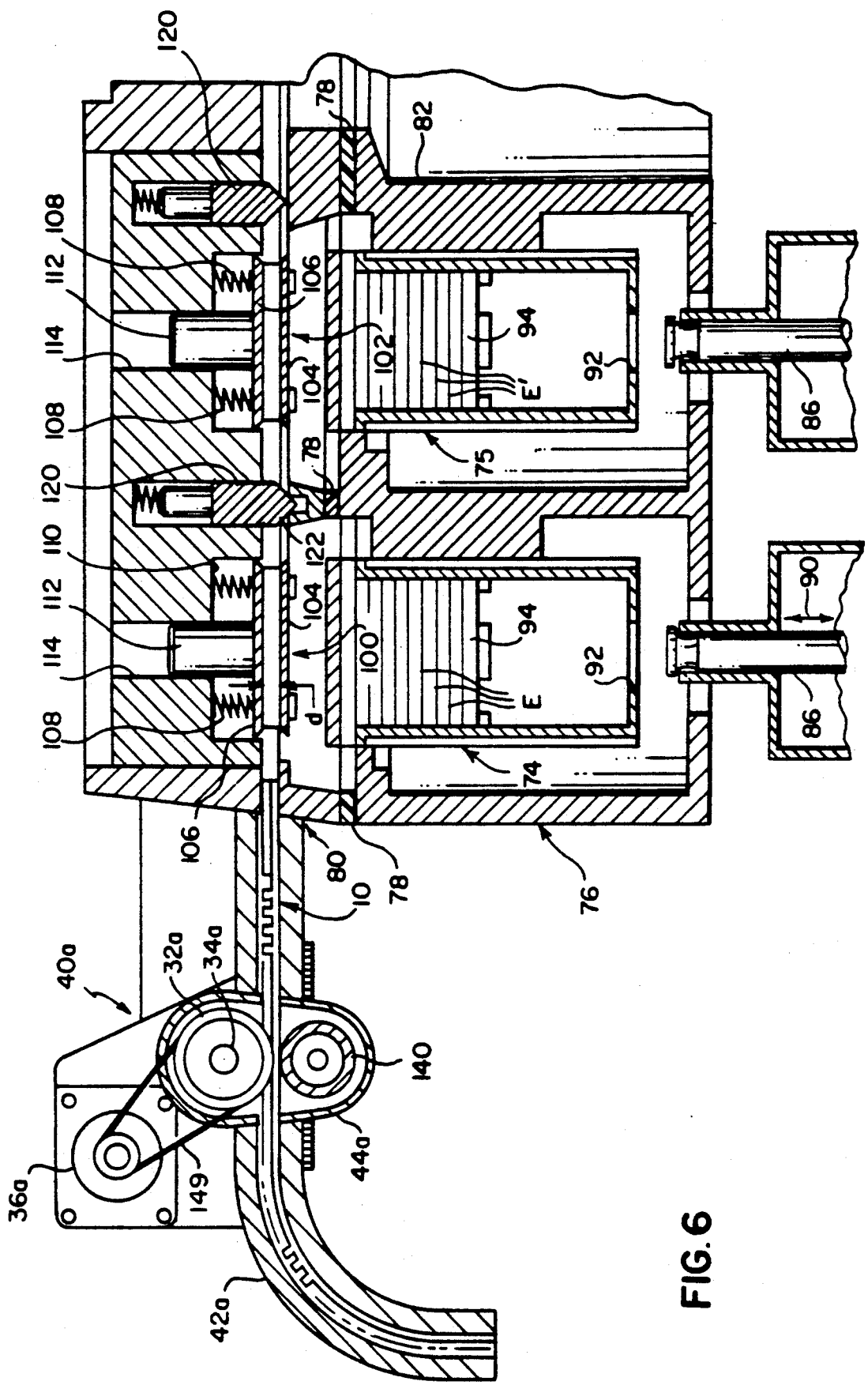
FIG. 6 is an elevational view similar to that of FIG. 5, illustrating more detail of an alternate embodiment.

The invention is described hereinafter in connection with a pusher blade used in a clinical analyzer, specifically to move a test element out of a stack of elements disposed in a particular arrangement. In addition, the invention is useful for the movement of a slide-type test element between any two locations, regardless of whether one of them is a stack of elements, and regardless of whether, if used with a stack of elements, such stacks come in adjacent pairs or are located in any particular place in an analyzer.

Orientations such as "up", "down", and "horizontal" are used in connection with the orientations of the parts during their normal use.

Referring to FIG. 1, the prior art pusher blade 160 shown in FIGS. 2 and 3 of U.S. Pat. No. 4,512,952 comprises a planar front pushing end 161, and a rear portion that is the driving portion. That driving portion is a precise-positioning drive that comprises a ridge 166 of substantial height, having on one of its exposed faces, ribs 167 that comprise the rack of a rack-and-pinion drive. These ribs 167 project away from ridge 166 in a direction 169 that is generally parallel to the overall plane of blade 160, that is, the plane of front end portion 161. The rack in turn is driven by a pinion 164. It will be readily appreciated that, in such a case, ridge 166 prevents the rear portion of blade 160 from being able to flex out of the plane occupied by the planar portion 161. As a result, therefore, there must be provided substantial run-out room in the direction of arrow 171, for the rear portion to extend as end 161 is withdrawn toward pinion 164.

The pusher blade 10, FIG. 2 of the invention, includes a test-element engaging end 12, an end 14 opposite to end 12, and a body portion 16 between and connecting such ends. Blade 10 has an upper surface 18 and an opposite lower surface 19. In accordance with the invention, end 12 is constructed to be relatively stiff, whereas body portion 16 and end 14 are constructed to be flexible. Preferably, they are sufficiently flexible as to readily bend without damage, that is, without exceeding its elastic limit, around a corner having a radius of curvature R which is no greater than about 20 cm. A preferred range for the radius of curvature is from 3 to 20 cm, with 4 cm being most Conversely, the relatively stiff portions of the blade are such as to exceed their elastic limit in bending about a radius of curvature that is less than about 20 cm.

Most preferably, the flexibility of the blade is achieved by molding it out of a relatively thin, flexible material, such as nylon, and by altering the construction of the rack, as detailed hereafter. Thickness "t", FIG. 4, of between about 0.7 mm and about 0.8 mm is particularly useful. materials are also advantageous because of their inexpensive cost.

To render end 12 relatively stiff or rigid, longitudinal ribs 20 are molded into that end on upper surface 18. Such ribs are two or three in number (as shown in FIGS. 2 and 3), and extend the direction of the primary length of the blade if laid flat, thus providing the stiffness. Preferably, the ribs terminate and are joined together adjacent body portion 16 at a transverse rib 22, FIG. 3.

Optionally, end 12 can include an aperture 23 extending transversely through it, FIG. 3, to allow a sensor to detect when end 12 is present and thus in position to initiate ejection of a test element.

To translate blade 10 forwards and backwards, driving means 30 are provided, along with a rack comprising associated transverse ribs 26 on the upper surface 18 of blade 10, FIG. 2. Driving means 30 comprise a pinion gear 32 mounted on a shaft 34, and a suitable motor 36, such as a stepper motor. In accordance with one aspect of the invention, the rack of the pusher blade is improved in that transverse ribs 26 extend upwardly away from upper surface 18 in a direction Z, FIG. 2, that is generally perpendicular to the overall plane of the blade, namely the plane of axes X and Y. Thus, the rack element can be readily formed as part of the molding of blade 10, without destroying flexibility. Ribs 26 are spaced apart a distance that mates with pinion gear 32.

It will be readily appreciated that ribs 26, by their extension in the direction Z instead of direction Y, FIG. 2, ensure that no rigidifying ridge needs to be added, such as would be an extension of rigidifying ribs 20. That is, preferably ribs 26 have a crown surface 27 and a root surface 28, wherein the root surface 28, FIG. 4, coincides with or is below surface 18. Alternatively, however, root surface 28 of ribs 26 could be raised slightly (not shown) from surface 18, so long as the overall flexibility, as defined by the bendability described above, is not destroyed.

A guide housing 40 is provided, FIG. 5, for receiving blade 10 and for bending it about radius R, preferably to form an approximate right-angle bend. Housing 40 also houses drive means 30. More specifically, upper portion 42 and lower portion 44 of housing 40 provide opposed wall surfaces, such as surfaces 46 and 48, that form a closed curved path 50 of radius R. Blade 10 reciprocates along this path, as shown, in response to the driving action of pinion 32. Housing 42 is shaped to accommodate pinion gear 32. The portion 52 of path 50 that extends beyond gear 32 towards the rest of the analyzer, is linear since it receives the stiff end 12 of blade 10 that will not bend.

Alternatively (not shown), the bend provided by radius R can be some angle considerably different from 90° C., for example 30° C. or 60° C. An approximate 90° C. bend is preferred, however, to curl the extension 14 of the blade 10 downwards (FIG. 5), thus minimizing the horizontal extension of the apparatus containing the blade.

In one use of the invention, stacks 60, 62 (FIG. 5) of test elements E and E' are disposed adjacent housing portion 52, to be operated upon by the pusher blade. Test elements E and E' can be ejected by blade 10 from one or the other stack, arrow 64, and transferred to other locations, such as a preheater platform 66 adjacent to an incubator 68. Any mechanism for positioning such stacks adjacent to housing portion 52 can be used, as well as any mechanism for raising and lowering the stacks (arrows 70, 72) to intersect the path of arrow 64.

A useful example of such mechanisms is described in U.S. Pat. No. 4,512,952 issued Apr. 23, 1985, the details of which are expressly incorporated herein by reference. Briefly, as shown in FIG. 6, such stacks can be disposed in cartridges 74 and 75 mounted in concentric rings on a rotor 76. Such rings can be connected to rotate together, as shown, or they can be independently mounted to rotate separately (not shown). Rotor 76 seals at bearing surfaces 78 against a stationary bridging member 80, and is driven by a suitable mechanism, (not shown) preferably attached at wall 82. The rotor rotates about an axis of rotation that is to the right or left of the stacks shown in FIG. 4. If it is to the right, the axis is preferably centered on incubator 68. Intermediate wall 77 separates the two stacks.

To raise and lower cartridges 74 or 75, a plunger 86 is provided at a station adjacent to blade housing 40A, associated with each of the Z rings that rotate above the plungers. (Parts similar to those shown in the previous embodiment of FIGS. 2-5 are given the same reference numeral to which the suffix "A" is appended.) The plungers are activated by a mechanism such as is shown in the aforesaid '952 patent, to move up and down, arrow 90, into and out of aperture 92 of a cartridge, to push against the follower element 94 used to prevent remaining elements E or E' from falling to the bottom of the cartridge.

Bridging member 80 is constructed to allow blade 10 to bridge over either cartridge 74 or 75 (whichever one is *not* dispensing a test element). To this end, a shuttle 100 is mounted above the position occupied by cartridge 74, and a separate shuttle 102 above the position occupied by cartridge 75, when either cartridge is otherwise in position to dispense a test element. Each shuttle comprises a bottom plate 104, a top plate 106 spaced from the bottom plate a distance "d" that will accommodate blade 10 and a test element E or E', a pair of compression springs 108 hanging the shuttle from upper surface 110, and a centering rod 112 that slides up and down in aperture 112 in surface 110. Springs 108 can be coil springs or leaf springs. Optionally, a spring-based sealing member 120 is provided between the shuttles, particularly if each ring of stacks is separately rotatable, to allow separate environments to be provided for the two rings. That is, each member 120, when sealed as shown in FIG. 6, prevents substantial intermixing of the two atmospheres for the stacks. Member 120 is tapered at 122 to allow a pushed test element and blade 10 to cam it upward, FIG. 7. Some atmosphere transfers between stacks at this time, but it is insubstantial compared to the total.

Figure 7:
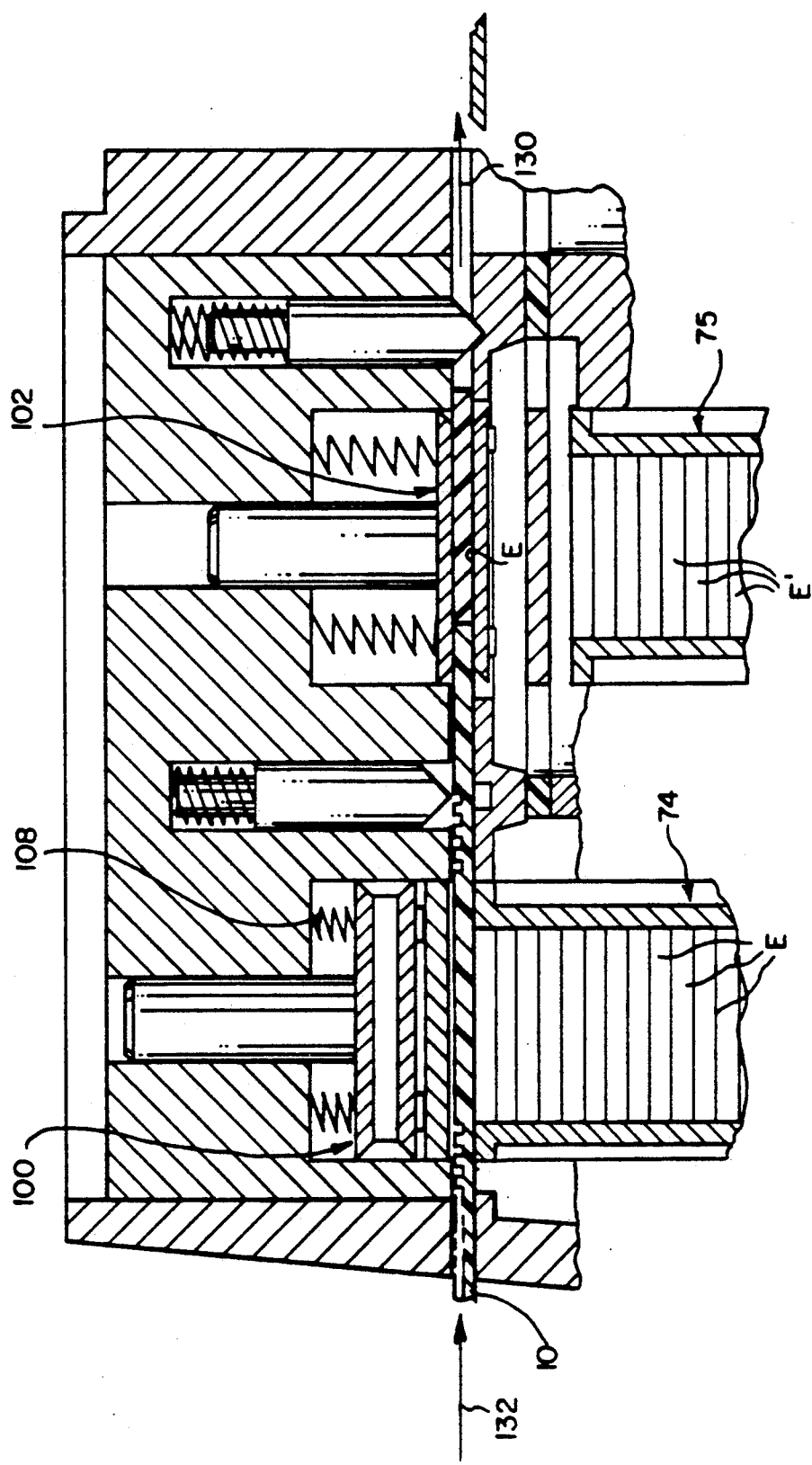
FIG. 7 is a fragmentary elevational view similar to that of FIG. 6, illustrating some of the parts in the next step of the operation wherein a test element is being moved by the pusher blade.

In operation, FIG. 7, the bridging member works by having a cartridge used to eject a test element, push its associated shuttle (shuttle 100 is pushed up by a cartridge 74 in this Figure) out of the way against spring 108, while the other shuttle (102 here) remains in place to bridge over the space under which cartridges 75 are located. Blade 10 is thus able to pass over both sets of rings of cartridges, and through cartridge 74, to eject element E towards preheater platform 66, arrow 130. Alternatively, only a cartridge 75 can be elevated against its shuttle 102, and blade 10 pushed, arrow 132, through shuttle 100 and into cartridge 75, to eject an element E'.

Any additional support can be provided in the blade housing besides that shown in FIG. 5. Thus, FIG. 6, a pinch roller 140 can be included in housing portion 44a, mounted opposite to the pinion gear 32a mounted in housing portion 42a of housing 40a. In this alternative embodiment, motor 36a is offset from drive shaft 34a and connected thereto by drive belt 149.

Figure 8:
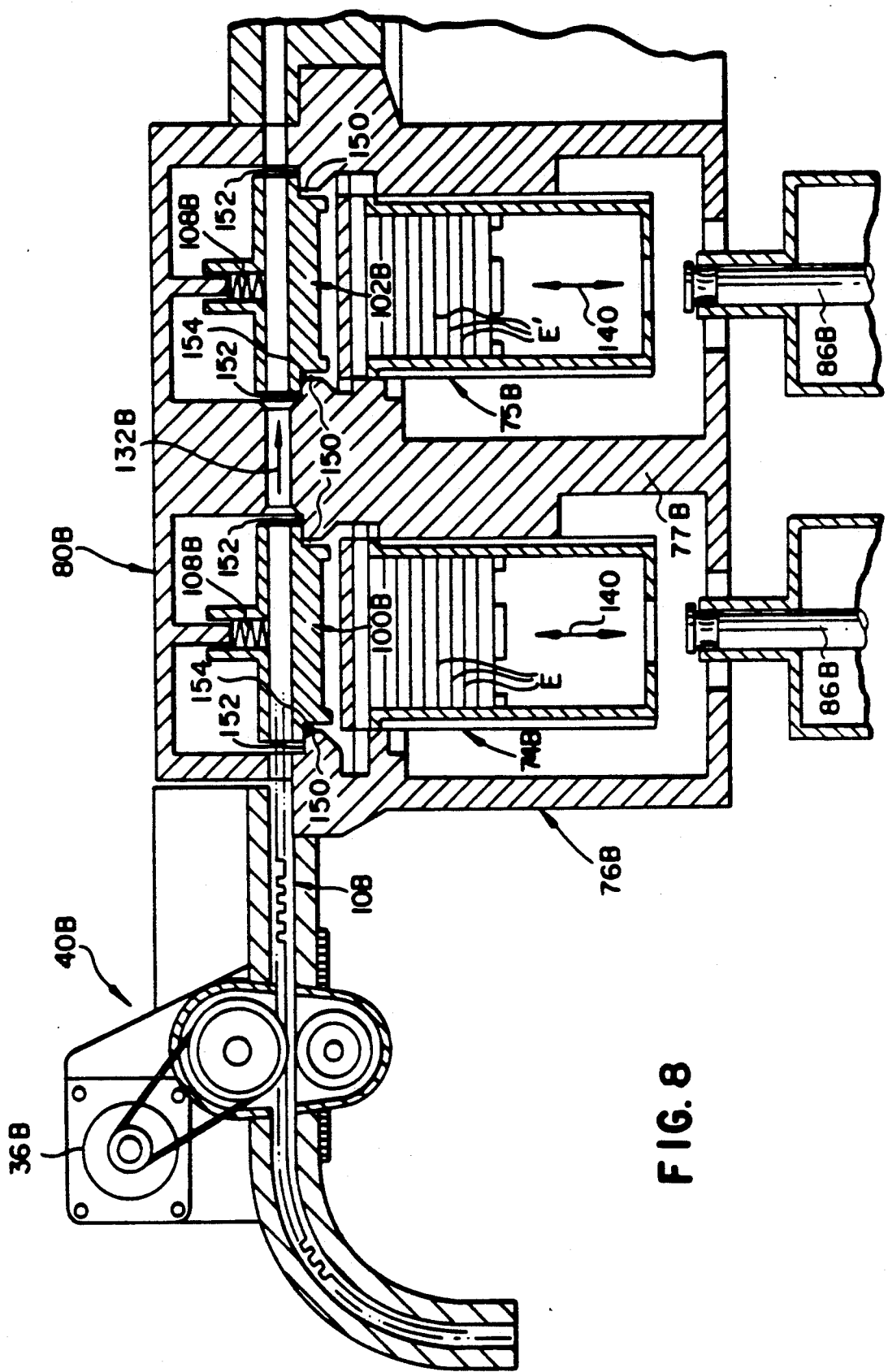
FIG. 8 is an elevational view similar to that of FIG. 6, but illustrating yet another embodiment.

It is not essential that the atmosphere intermixing-preventing seals between the two stacks be the type that has to be cammed out of the way by the pusher blade. An alternative is shown in FIG. 8. Parts similar to those previously described bear the same reference numerals, to which the distinguishing suffix B is appended.

Thus, housing 40B has a pusher blade 10B driven by motor 36B, and either cartridge 74B or 75B is elevated, arrows 140, into the path 132B of the blade by plungers 86B, as before. Rotor 76B allows two rows of cartridges to be rotated into the position shown in FIG. 8; and wall 77B keeps the two rows of cartridges separate. Bridging member 80B covers the cartridges and provides the bridging means for path 132B, generally as before. That is, displaceable shuttle member 100B and 102B allow a cartridge to be inserted into path 132B, or alternatively act as the guide for blade 10B and, for shuttle 102B, also for a test element E.

However, unlike the previous embodiment, no separate, cammable sealing means is required in bridging member 80B between shuttles 100B and 102B. Instead, the shuttle members themselves act to prevent intermixing of the atmospheres. That is, member 80B is provided with apertures 150 into which a cartridge is insertable by rod 86B. Each of these has a sealing seat 152 surrounding it, which mates with the annular undersurface 154 of either shuttle 100B or 102B, when the shuttle is in the "down" position, as shown. Springs 108B bias shuttle members 100B and 102B downwardly, as before, to seal on seats 152. When a shuttle is raised by a cartridge from seat 152, there is a slight release of atmosphere from one side of rotor 76 to the other, over wall 77B, but this is unsubstantial.

Figure 9:
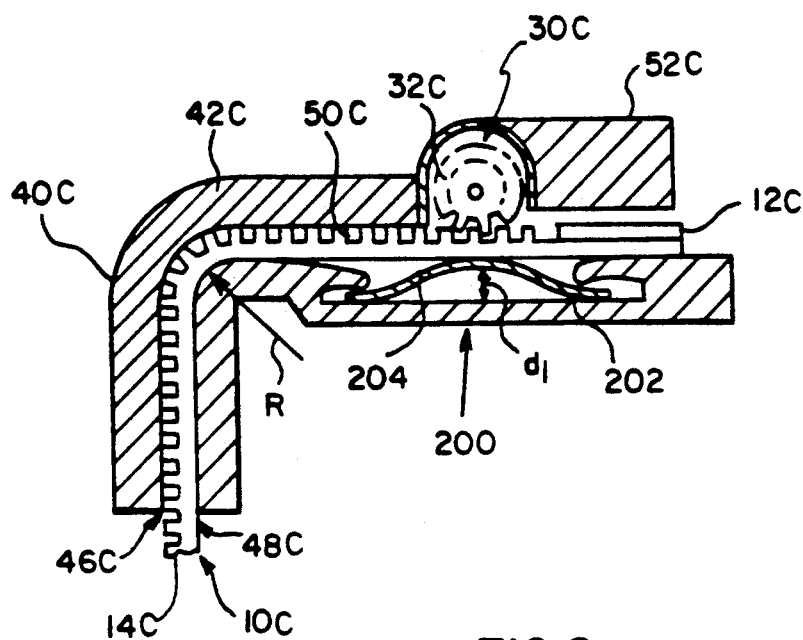
FIGS. 9 and 10 are fragmentary views similar to FIG. 5, but illustrating still another embodiment.
Figure 10:
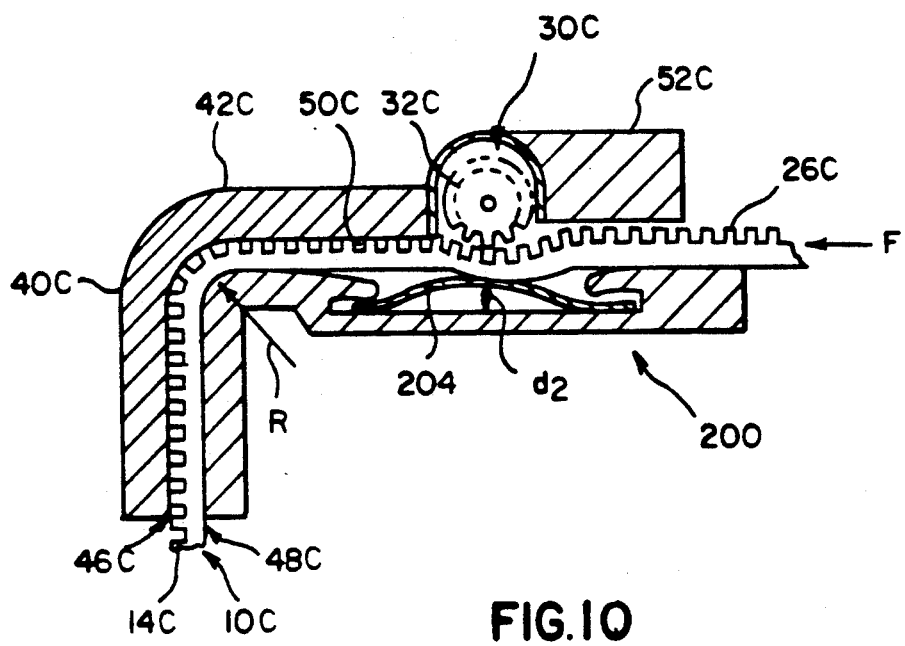

In most instances, the dispense blade mechanism described above functions very well to transfer the test elements as described. In rare instances, however, the relatively rigid backing member for the blade, e.g., housing 44 or roller 140, FIGS. 5 and 6, will cause the blade to become damaged if a jam occurs. That is, a test element can become jammed after it is pushed out of, e.g., a cartridge. The resulting increase in resistance force against the blade will damage the blade if motor 36 or 36a continues to drive. FIGS. 9 and 10 provide an embodiment that avoids this problem. Parts similar to those previously described bear the same reference numeral, to which the distinguishing suffix C is appended.

Thus, FIG. 9, blade 10C is housed in housing 40C and driven by driving means 30C as before, with all but end 12C of the blade being flexible. Thus, blade 10C follows a curved path 50C as described heretofore. However, the back-up member includes a clutch 200, which releases its pressure pushing blade 10C into contact with pinion gear 32C, in the event a jam occurs at end 12C. More specifically, clutch 200 is preferably a spring 202, such as a leaf spring under compression, with a projecting portion 204 that pushes blade 10C against pinion gear 32C with sufficient force to normally keep the blade engaged. A useful example of the force of spring portion 204 is about 6.7 newtons (1.5 lbs. of force). This leaves portion 204 spaced a distance $d_1$ from its housing.

Clutch 200 functions as follows, FIG. 10: If a jam occurs so that a resistance force F in excess of the spring force. e.g., 6.7 newtons (1.5 lbs.) occurs, then spring 202 buckles sufficiently to reduce distance $d_1$ to $d_2$, allowing the flexible blade 10C to itself buckle a sufficient distance as to disengage ribs 26C from pinion gear 32C. As a result, pinion gear 32C can continue to turn without permanently bending blade 10C or breaking off any of the ribs on the blade or the teeth on pinion gear 32C.

A variety of stations can be positioned downstream of the bridging member over stacks 60 and 62, into which a slide test element is accurately positioned by the pusher blade of the invention. Another, and a preferred embodiment is shown in FIG. 11, in which parts similar to those previously described bear the same reference numeral to which the distinguishing suffix "D" is appended.

Thus, as in the previous embodiment, a guide housing 40 is provided, FIG. 11, for guiding blade 10D to bend about radius R, preferably to form an approximate right-angle bend. Housing 40D also houses drive means 30D, and upper portion 42D and lower portion 44 of housing 40 provide opposed wall surfaces 46D and 48D, that form a closed curved path 50D of radius R. Blade 10D reciprocates along this path in response to the driving action of pinion 32D. Housing 42D is shaped to accommodate pinion gear 32D. Stacks 60D, 62D of test element E and E' are disposed adjacent housing portion 52D, to be operated upon by the pusher blade. Test elements E and E' are ejected by blade 10D from one or the other stack, arrow 64D. However, in this embodiment, the next station to which the elements are transferred is a liquid-dispensing station 266, interposed between stack 62D and incubator 68D. Such a station conventionally comprises a slot 270 for a slide element E or E', and a boss 272 apertured at least 274 to receive a pipette tip T to dispense sample liquid and/or reference fluid onto the element in slot 270. Thereafter, element E or E' is pushed into incubator 68D.

The invention has been described in detail with particular reference to certain preferred embodiments thereof, but it will be understood that variations and modifications can be effected within the spirit and scope of the invention.

What is claimed is:

1. In a chemical analyzer comprising a source of test elements to analyze liquid and a pusher blade to push test elements,
   the improvement wherein said pusher blade comprises a first end portion shaped to push a test element,
   a second end portion opposite to said first end portion,
   and a body portion between said end portions, said body portion further comprising a strip including a rack gear for engaging a pinion gear in a drive mechanism for said blade, said rack gear comprising ribs extending out of said first strip in a direction that is generally perpendicular to the overall plane of said first end portion,
   at least said body portion and said second end portion being sufficiently flexible as to bend without exceeding its elastic limit, about a radius of curvature of not greater than about 20 cm,
   and further including in said blade, end-detecting means for generating a sensing signal indicative of said end portion being present at a particular location.

2. An analyzer as defined in claim 1, and further including guide means for guiding said body and said second end around said radius of curvature,
   whereby said second end is directed to occupy a plane that is skewed to the plane occupied by said first end.

3. An analyzer as defined in claim 2, and further including means for locating a stack of test elements adjacent said guide means and in position to cause said stiff end portion to engage a test element in said stack to remove said engaged element from the stack.

4. An analyzer as defined in claim 1, 2 or 3, and further including guide means for directing said body portion and said second end portion of said blade to move around said radius and said stiff end to reciprocate along a linear path.

5. An analyzer as defined in claim 4, and further including means for locating two stacks of test elements in a row along said linear path, said guide means being effective to guide said blade stiff end into engagement with a test element in on or the other said stacks.

6. An analyzer as defined in claim 5, wherein said stack-locating means comprise housing means that separate one stack from the other,
   and further including means for preventing substantial intermixing of the separate environments of said separated stacks when said blade stiff end is guided by said means into engagement with either of said stacks.

7. An analyzer as defined in claim 3, and further including a liquid-dispensing station adjacent to said stack-locating means into which a test element is pushed by said pusher blade.

8. In a chemical analyzer comprising a source of test elements to analyze liquid and a housing for a pusher blade to push test elements,
   the improvement wherein said housing comprises opposing guiding walls defining a path of travel for a pusher blade having a rack gear therein, said walls being shaped to define an approximately right-angled bend in such path, and means in said housing for driving said blade, said drive means including a pinion gear that engages a blade to be driven by said means.

9. An analyzer as defined in claim 8, wherein said bend forms approximately a right-angle.

10. An analyzer as defined in claim 8 or 9, wherein the radius of curvature of said bend is about 4 cm.

11. An analyzer as defined in claim 8 or 9, and further including a pusher blade constructed to move within said path in response to said driving means, said pusher blade including a body portion that is sufficiently flexible as to bend without exceeding its elastic limit about a radius of curvature of not greater than about 20 cm, so as to negotiate said bend in said path.

12. An analyzer as defined in claim 8 or 9, and further including a pusher blade constructed to move within said path in response to said driving means, said pusher blade including a body portion that is sufficiently flexible as to bend without exceeding its elastic limit about a radius of curvature of not greater than about 20 cm, so as negotiate said bend in said path, said body portion including ribs that extend out of said body portion in a direction that is generally perpendicular to the overall plane of said pusher blade.

13. In a chemical analyzer comprising a source of test elements to analyze liquid and a pusher blade to push test elements,
   the improvement wherein said first pusher blade comprises a first end portion shaped to push a test element,
   a second end portion opposite to said first end portion,
   and a body portion between said end portions, said body portion further comprising a strip including a rack gear for engaging a pinion gear in a drive mechanism for said blade, said rack gear comprising ribs extending out of said strip in a direction that is generally perpendicular to the overall plane of said first end portion,
   at least said body portion and said second end portion being sufficiently flexible as to bend without exceeding its elastic limit, about a radius of curvature of not greater than about 20 cm,
and further including in said blade, end-detecting means for generating a sensing signal indicative of said end portion being present at a particular location, said generating means comprising an aperture in said blade closely adjacent to said first end portion.

* * * * *

UNITED STATES PATENT AND TRADEMARK OFFICE
CERTIFICATE OF CORRECTION

PATENT NO. : 5,330,716 Page 1 of 2

DATED : July 19, 1994

INVENTOR(S) : James D. Shaw, Martin F. Muszak, David A. Heavner

It is certified that error appears in the above-indentified patent and that said Letters Patent is hereby corrected as shown below:

Claim 1 - Column 7, Line 44
Delete "said first strip" and insert therefor --said strip--.

Column 7, Line 53
Delete "said end portion" and insert therefor --said first end portion--.

Claim 2 - Column 7, Line 56
Delete "guiding said body," and insert therefor --guiding said body portion--.

Column 7, Line 57
Delete "second end" and insert therefor --second end portion--.

Column 7, Line 58
Delete "said second end" and insert therefor --said second end portion--.

Column 7, Line 60
Delete "first end" and insert therefor --first end portion--.

Claim 3 - Column 7, Lines 63-64
Delete "said stiff end portion" and insert therefor --said first end portion--.

Claim 4 - Column 8, Line 1
Delete "said stiff end" and insert therefor --said first end portion--.

UNITED STATES PATENT AND TRADEMARK OFFICE
CERTIFICATE OF CORRECTION

PATENT NO. : 5,330,716
DATED : July 19, 1994
INVENTOR(S) : James D. Shaw, Martin F. Muszak, David A. Heavner It is certified that error appears in the above-indentified patent and that said Letters Patent is hereby corrected as shown below:

Claim 5 - Column 8, Line 6
  Delete "said ... stiff end into" and insert therefor
--said ... first end portion into--.

Claim 6 - Column 8, Line 13
  Delete "said ... stiff end" and insert therefor
--said ... first end portion--.

Signed and Sealed this

Fifteenth Day of August, 1995

Attest:

BRUCE LEHMAN

*Attesting Officer*  Commissioner of Patents and Trademarks